US009119896B2

(12) United States Patent
Hissong et al.

(10) Patent No.: US 9,119,896 B2
(45) Date of Patent: *Sep. 1, 2015

(54) POLYMERIC SEALANT FOR MEDICAL USE

(75) Inventors: James Britton Hissong, Jacksonville, FL (US); Dana A. Oliver, Jacksonville, FL (US); Cecil O. Lewis, Jacksonville, FL (US); Janis Saunier, Ponte Vedra Beach, FL (US); Matthew F. Myntti, St. Augustine, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,636

(22) Filed: Dec. 12, 2011

(65) Prior Publication Data

US 2012/0184926 A1    Jul. 19, 2012

Related U.S. Application Data

(62) Division of application No. 11/704,115, filed on Feb. 8, 2007, now Pat. No. 8,088,095.

(51) Int. Cl.
*A61M 35/00* (2006.01)
*A61L 24/00* (2006.01)
*A61L 24/10* (2006.01)
*A61L 31/04* (2006.01)
*A61L 31/14* (2006.01)
*A61L 31/16* (2006.01)

(52) U.S. Cl.
CPC ......... *A61L 24/0015* (2013.01); *A61L 24/0042* (2013.01); *A61L 24/108* (2013.01); *A61L 31/047* (2013.01); *A61L 31/148* (2013.01); *A61L 31/16* (2013.01); *A61L 2300/404* (2013.01); *A61L 2300/41* (2013.01); *A61L 2300/416* (2013.01)

(58) Field of Classification Search
CPC ............ A61L 24/0015; A61L 24/0042; A61L 24/108; A61L 31/047; A61L 31/148; A61L 31/16; A61L 2300/404; A61L 2300/416
See application file for complete search history.

(56) References Cited

U.S. PATENT DOCUMENTS

| | | |
|---|---|---|
| 3,422,186 A | 1/1969 | Sasmor |
| 4,002,775 A | 1/1977 | Kabara |
| 4,107,328 A | 8/1978 | Michaels |
| 4,323,551 A | 4/1982 | Parran, Jr. |
| 4,427,650 A | 1/1984 | Stroetmann |
| 4,427,651 A | 1/1984 | Stroetmann |
| 4,442,655 A | 4/1984 | Stroetmann |
| 4,662,829 A | 5/1987 | Nehring |
| 4,851,521 A | 7/1989 | Della Valle et al. |
| 4,902,281 A | 2/1990 | Avoy |
| 5,017,229 A | 5/1991 | Burns et al. |
| 5,145,664 A | 9/1992 | Thompson |
| 5,166,331 A | 11/1992 | Della Valle et al. |
| 5,208,257 A | 5/1993 | Kabara |
| 5,229,103 A | 7/1993 | Eagle et al. |
| 5,246,964 A | 9/1993 | Ueno |
| 5,290,552 A | 3/1994 | Sierra et al. |
| 5,326,567 A | 7/1994 | Capelli |
| 5,336,163 A | 8/1994 | DeMane et al. |
| 5,388,574 A * | 2/1995 | Ingebrethsen ........... 128/203.17 |
| 5,442,053 A | 8/1995 | Della Valle et al. |
| 5,480,658 A | 1/1996 | Melman |
| 5,575,815 A | 11/1996 | Slepian et al. |
| 5,601,594 A | 2/1997 | Best |
| 5,631,241 A | 5/1997 | Della Valle et al. |
| 5,644,049 A | 7/1997 | Giusti et al. |
| 5,662,913 A | 9/1997 | Capelli |
| 5,676,964 A | 10/1997 | Della Valle et al. |
| 5,693,065 A | 12/1997 | Rains, III |
| 5,709,546 A | 1/1998 | Waggoner |
| 5,716,981 A | 2/1998 | Hunter et al. |
| 5,739,176 A | 4/1998 | Dunn et al. |
| 5,763,410 A | 6/1998 | Edwardson et al. |
| 5,773,033 A | 6/1998 | Cochrum et al. |
| 5,895,781 A | 4/1999 | Neumiller et al. |
| 5,910,420 A | 6/1999 | Tuompo et al. |
| 5,925,334 A | 7/1999 | Rubin et al. |
| 5,968,542 A | 10/1999 | Tipton |
| 6,001,870 A | 12/1999 | Henkel |
| 6,013,657 A | 1/2000 | Lavon et al. |
| 6,063,061 A | 5/2000 | Wallace et al. |
| 6,071,305 A | 6/2000 | Brown et al. |

(Continued)

FOREIGN PATENT DOCUMENTS

EP    0 530 861 B1    3/1993
EP    1 374 856 A1    1/2004

(Continued)

OTHER PUBLICATIONS

Gross CW, et al. 2001. Autologous Fibrin Sealant Reduces Pain After Tonsillectomy. The Laryngoscope; 111: 259-263.*
Post, J.C., "Direct evidence of bacterial biofilms in otitis media", Laryngoscope 111(12):2083-94 (2001).
Ehrlich et al., "Mucosal Biofilm Formation on Middle-Ear Mucosa in the Chinchilla Model of Otitis Media", JAMA 287(13):1710-15 (2002).
Fergie, N. et al., "Is otitis media with effusion a biofilm infection?", Clin Otolaryngol Allied Sci. 29(1):38-46 (2004).
Ferguson B.J. and Stolz D.B., "Demonstration of biofilm in human bacterial chronic rhinosinusitis", Am J Rhinol 19:452-457, 2005.
Ramadan H.H., Sanclement J.A. and Thomas J.G., "Chronic rhinosinusitis and biofilms", Otolaryngol Head Neck Surg. 132:414-417, 2005.

(Continued)

*Primary Examiner* — Carlos Azpuru
*Assistant Examiner* — David Browe
(74) *Attorney, Agent, or Firm* — IPLM Group, P.A.

(57) ABSTRACT

The invention provides a polymeric medical sealant. The medical sealant is useful for application to the tonsils and adenoids, wherein the sealant performs at least one of the following functions, a) inhibit the colonization of bacteria, b) inhibit the binding of bacteria to tissue, c) reduction of tissue morbidity, d) hemostasis, e) coating and protection of tissue during healing. f) promotion of healing, and g) reduction of pain.

25 Claims, No Drawings

(56) References Cited

U.S. PATENT DOCUMENTS

| | | | |
|---|---|---|---|
| 6,129,761 A | 10/2000 | Hubbell | |
| 6,143,330 A | 11/2000 | Aaltonen et al. | |
| 6,156,294 A | 12/2000 | Mautone | |
| 6,156,792 A | 12/2000 | Hatton et al. | |
| 6,200,587 B1 * | 3/2001 | Soe et al. | 424/423 |
| 6,203,822 B1 | 3/2001 | Schlesinger et al. | |
| 6,224,857 B1 | 5/2001 | Romeo et al. | |
| 6,248,371 B1 | 6/2001 | Domenico | |
| 6,284,804 B1 | 9/2001 | Singh et al. | |
| 6,312,725 B1 | 11/2001 | Wallace | |
| 6,342,251 B1 | 1/2002 | Illum et al. | |
| 6,372,229 B1 | 4/2002 | Ollerenshaw et al. | |
| 6,375,963 B1 | 4/2002 | Repka et al. | |
| 6,395,295 B1 | 5/2002 | Hills et al. | |
| 6,395,746 B1 | 5/2002 | Cagle et al. | |
| 6,423,333 B1 | 7/2002 | Stedronsky et al. | |
| 6,423,694 B1 | 7/2002 | Drutz et al. | |
| 6,533,749 B1 | 3/2003 | Mitusina et al. | |
| 6,541,116 B2 | 4/2003 | Michal et al. | |
| 6,541,460 B2 | 4/2003 | Petito | |
| 6,610,314 B2 | 8/2003 | Koenig et al. | |
| 6,613,084 B2 | 9/2003 | Yang | |
| 6,616,913 B1 | 9/2003 | Mautone | |
| 6,623,513 B2 | 9/2003 | Biel | |
| 6,623,521 B2 | 9/2003 | Steinke et al. | |
| 6,632,457 B1 | 10/2003 | Sawhney | |
| 6,676,930 B2 | 1/2004 | Mautone | |
| 6,685,697 B1 | 2/2004 | Arenberg et al. | |
| 6,686,346 B2 | 2/2004 | Nilsson et al. | |
| 6,706,290 B1 | 3/2004 | Kajander et al. | |
| 6,723,709 B1 | 4/2004 | Pressato et al. | |
| 6,762,160 B2 | 7/2004 | Barbeau et al. | |
| 6,770,729 B2 | 8/2004 | Van Antwerp | |
| 6,812,196 B2 | 11/2004 | Rees et al. | |
| 6,855,678 B2 | 2/2005 | Whiteley | |
| 6,867,233 B2 | 3/2005 | Roselle et al. | |
| 6,869,938 B1 | 3/2005 | Schwartz et al. | |
| 6,891,037 B1 | 5/2005 | Hasler et al. | |
| 6,919,348 B2 | 7/2005 | Wei | |
| 6,936,579 B2 | 8/2005 | Urban | |
| 6,953,772 B2 | 10/2005 | Lopes | |
| 6,962,813 B2 | 11/2005 | Pier et al. | |
| 6,989,195 B2 | 1/2006 | Anderson | |
| 7,090,882 B2 | 8/2006 | Koefod et al. | |
| 7,119,217 B2 | 10/2006 | Jiang et al. | |
| 7,128,897 B2 | 10/2006 | Osbakken et al. | |
| 7,220,431 B2 | 5/2007 | Sawchuk et al. | |
| 7,238,363 B2 | 7/2007 | Mansouri et al. | |
| 7,244,841 B2 | 7/2007 | Love et al. | |
| 7,341,983 B2 | 3/2008 | Pedersen et al. | |
| 7,410,480 B2 | 8/2008 | Muni et al. | |
| 7,446,089 B2 | 11/2008 | Singh et al. | |
| 7,494,963 B2 | 2/2009 | Ahmed et al. | |
| 7,544,192 B2 | 6/2009 | Eaton et al. | |
| 7,714,011 B2 | 5/2010 | Clarot et al. | |
| 7,976,875 B2 | 7/2011 | Myntti | |
| 8,044,156 B2 | 10/2011 | Tamareselvy et al. | |
| 8,062,246 B2 | 11/2011 | Moutafis et al. | |
| 2001/0044651 A1 | 11/2001 | Steinke et al. | |
| 2001/0051613 A1 | 12/2001 | Illum et al. | |
| 2002/0022588 A1 | 2/2002 | Wilkie et al. | |
| 2002/0029015 A1 | 3/2002 | Camenzind et al. | |
| 2002/0055158 A1 | 5/2002 | Greene et al. | |
| 2002/0187918 A1 | 12/2002 | Urban | |
| 2003/0009213 A1 | 1/2003 | Yang | |
| 2003/0062147 A1 | 4/2003 | Schoen et al. | |
| 2003/0079758 A1 | 5/2003 | Siegel et al. | |
| 2003/0083219 A1 | 5/2003 | Rees et al. | |
| 2003/0133883 A1 | 7/2003 | Finnegan et al. | |
| 2003/0139382 A1 | 7/2003 | Wall et al. | |
| 2003/0157687 A1 | 8/2003 | Greene et al. | |
| 2003/0199969 A1 | 10/2003 | Steinke et al. | |
| 2003/0235602 A1 | 12/2003 | Schwarz | |
| 2004/0101506 A1 | 5/2004 | Fust | |
| 2004/0106987 A1 | 6/2004 | Palasis et al. | |
| 2004/0110738 A1 | 6/2004 | Gillis et al. | |
| 2004/0116958 A1 | 6/2004 | Gopferich et al. | |
| 2004/0117006 A1 | 6/2004 | Lewis et al. | |
| 2004/0143001 A1 | 7/2004 | Love et al. | |
| 2004/0204399 A1 | 10/2004 | Oshbakken et al. | |
| 2004/0213758 A1 | 10/2004 | Sefton et al. | |
| 2004/0214753 A1 | 10/2004 | Britten et al. | |
| 2005/0003007 A1 | 1/2005 | Boix et al. | |
| 2005/0032668 A1 | 2/2005 | Pedersen et al. | |
| 2005/0042240 A1 | 2/2005 | Utterberg et al. | |
| 2005/0043706 A1 | 2/2005 | Eaton et al. | |
| 2005/0064508 A1 | 3/2005 | Belcher et al. | |
| 2005/0080396 A1 | 4/2005 | Rontal | |
| 2005/0106728 A1 | 5/2005 | Burgess et al. | |
| 2005/0147679 A1 | 7/2005 | Petito et al. | |
| 2005/0220895 A1 | 10/2005 | Bucalo et al. | |
| 2005/0226937 A1 | 10/2005 | O'Hagen et al. | |
| 2005/0244339 A1 | 11/2005 | Jauering et al. | |
| 2005/0282722 A1 | 12/2005 | McReynolds et al. | |
| 2006/0003008 A1 | 1/2006 | Gibson et al. | |
| 2006/0018945 A1 | 1/2006 | Britigan et al. | |
| 2006/0035808 A1 | 2/2006 | Ahmed et al. | |
| 2006/0045850 A1 | 3/2006 | Namburi et al. | |
| 2006/0051385 A1 | 3/2006 | Scholz | |
| 2006/0106361 A1 | 5/2006 | Muni et al. | |
| 2006/0205621 A1 | 9/2006 | Borazjani et al. | |
| 2006/0210605 A1 | 9/2006 | Chang et al. | |
| 2007/0207192 A1 | 9/2007 | Holl et al. | |
| 2007/0264226 A1 | 11/2007 | Karagoezian et al. | |
| 2007/0264310 A1 | 11/2007 | Hissong et al. | |
| 2007/0264342 A1 | 11/2007 | Oliver et al. | |
| 2007/0264353 A1 | 11/2007 | Myntti et al. | |
| 2008/0010947 A1 | 1/2008 | Huang et al. | |
| 2008/0248558 A1 | 10/2008 | Deinhammer et al. | |
| 2009/0005339 A1 | 1/2009 | Scholz et al. | |
| 2010/0240770 A1 | 9/2010 | Qi et al. | |

FOREIGN PATENT DOCUMENTS

| | | | |
|---|---|---|---|
| FR | 2 710 529 A1 | 4/1995 | |
| JP | 52-007428 | 1/1977 | |
| RU | 2 125 432 C1 | 1/1999 | |
| RU | 222 8203 | 5/2004 | |
| SU | 1128917 A1 | 12/1984 | |
| SU | 1699430 A1 | 12/1991 | |
| WO | WO 92/16245 | 10/1992 | |
| WO | WO 94/05330 | 3/1994 | |
| WO | WO 95/03036 | 2/1995 | |
| WO | WO 97/38698 | 10/1997 | |
| WO | WO 98/09622 | 3/1998 | |
| WO | WO 99/27905 A | 6/1999 | |
| WO | WO 00/21510 | 4/2000 | |
| WO | WO 00/56283 | 9/2000 | |
| WO | WO 03/061579 A2 | 7/2003 | |
| WO | WO 03/092745 A1 | 11/2003 | |
| WO | WO 2004/009143 A1 | 1/2004 | |
| WO | WO 2004/024187 A2 | 3/2004 | |
| WO | WO 2004/087227 * | 10/2004 | A61L 15/22 |
| WO | WO 2005/000029 A2 | 1/2005 | |
| WO | WO 2005/089670 A1 | 9/2005 | |
| WO | WO 2006/099386 A2 | 9/2006 | |
| WO | WO 2008/097317 A1 | 8/2008 | |

OTHER PUBLICATIONS

Benninger M.S., Ferguson B.J., Hadley J.A., et al., "Adult chronic rhinosinusitis: Definitions, diagnosis, epidemiology, and pathophysiology", Otolaryngol Head Neck Surg 129 (3 suppl):S1-S32, 2003.

Nadel D.M., Lanza D.C., and Kennedy D.W., "Endoscopically guided cultures in chronic sinusitis", Am J Rhinol 12:233-241, 1998.

Stepanovic S, Vukovic D, Dakic I, et al., "A modified microtiter-plate test for quantification of staphylococcal biofilm formation", J Microbiol Methods 40:175-179, 2000.

Gotz F., "Staphylococcus and biofilms", Mol Microbiol 43:1367-1378, 2002.

Lethbridge-Çejku M, Rose D, Vickerie J. Summary health statistics for US adults: National Health Interview Survey, 2004. National

(56) References Cited

OTHER PUBLICATIONS

Center for Health Statistics. Vital Health Stat 2006;10 (228). Available: http://www.cdc.gov/nchs/fastats/sinuses.htm.
Rosiak, J.M. et al., "Radiation Formation of Hydrogels for Biomedical Purposes. Some Remarks and Comments", Radiat. Phys. Chem. vol. 46, No. 2, pp. 161-168, 1995.
Costerton J.W., Stewart P.S. and Greenberg E.P., "Bacterial biofilms: A common cause of persistent infections", Science 284:1318-1322, 1999.
Morris D.P. and Hagr A., "Biofilm: Why the sudden interest?" J Otolaryngol 34(suppl 2):S56-S5, 2005.
Hall-Stoodley L, Hu F.Z., Gieseke A, et al., "Direct detection of bacterial biofilms on the middle-ear mucosa of children with chronic otitis media." JAMA 296:202-211, 2006.
Sanderson A.R., Leid J.G., and Hunsaker D., "Bacterial biofilms on the sinus mucosa of human subjects with chronic rhinosinusitis", Laryngoscope 116:1121-1126 (2006).
Sanclement J.A., Webster P., Thomas J., and Ramadan H.H., "Bacterial biofilms in surgical specimens of patients with chronic rhinosinusitis", Laryngoscope 115:578-582, 2005.
Bendouah Z., Barbeau J., Hamad W.A., and Desrosiers M., "Biofilm formation by *Staphylococcus aureus* and *Pseudomonas aeruginosa* is associated with an unfavorable evolution after surgery for chronic sinusitis and nasal polyposis", Otolaryngol Head Neck Surg. 134:991-996, 2006.
Bhattacharyya N., and Kepnes L.J., "The microbiology of recurrent rhinosinusitis after endoscopic sinus surgery", Arch Otolaryngol Head Neck Surg. 125:1117-1120, 1999.
Cryer J., Schipor I., Perloff J.R., and Palmer J.N., "Evidence of bacterial biofilms in human chronic sinusitis", ORL J Otorhinolaryngol Relat Spec 66:155-158, 2004.
Meltzer E.O., Hamilos D.L., Hadley J.A., et al., "Rhinosinusitis: Establishing definitions for clinical research and patient care", J Allergy Clin Immunol 114(suppl):S155-S212, 2004.
Chiu A.G., and Kennedy D.W., "Surgical management of chronic rhinosinusitis and nasal polyposis: a review of the evidence", Curr Allergy Asthma Rep 4:486-489, 2004.
Bhattacharyya N., "Clinical outcomes after endoscopic sinus surgery", Curr Opin Allergy Clin Immunol 6:167-171, 2006.
Wormald P.J., Psaltis A., and Ha K., "A sheep model for the study of biofilms in sinusitis", In Programs and abstracts of the 52nd Annual Meeting of the American Rhinologic Society, Toronto, Ontario, Canada, Sep. 16, 2006.
Anglen J.O., Apostoles S., Christensen G., and Gainor B., "The efficacy of various irrigation solutions in removing slime-producing Staphylococcus", J Orthop Trauma 8:390-396, 1994.
Chole, Richard A. and Faddis, Brian T., Evidence for Microbial Biofilms in Cholesteatomas, Arch Otolaryngol Head and Neck Surg. 2002; 128: 1129-1133. Downloaded Apr. 17, 2007 from Medtronic Xomed at www.archoto.com.
Desrosiers M. Refractory chronic rhinosinusitis: pathophysiology and management of chronic rhinosinusitis persisting after endoscopic sinus surgery. Curr Allergy Asthma Rep 2004;4:200-7.
Smith TL, Batra PS, Seiden AM, Hannley M. Evidence supporting endoscopic sinus surgery in the management of adult chronic sinusitis: a systematic review. Am J Rhinol 2005;19:537-43.
Perloff JR, Palmer JN. Evidence of bacterial biofilms on frontal recess stents in patients with chronic rhinosinusitis. Am J Rhinol 2004;18:377-80.
Wright ED, Frenkiel S. Infectious adult rhinosinusitis: etiology, diagnosis, and management principles. J Otolaryngol 2005;34(suppl 1):S7-13.
Luong A, Marple BF. Sinus surgery: indications and techniques. Clin Rev Allergy Immunol 2006;30:217-22.
Abdi-Ali A, Mohammadi-Mehr M, Agha Alaei Y. Bactericidal activity of various antibiotics against biofilm-producing *Pseudomonas aeruginosa*. Int J Antimicrob Agents 2206;27:196-200.
Jefferson KK, Goldmann DA, Pier GB. Use of confocal microscopy to analyze the rate of vancomycin penetration through *Staphylococcus aureus* biofilms. Antimicrob Agents Chemother 2005;49:2467-73.
Walters MC 3rd, Roe F, Bugnicourt A, Franklin MJ, Stewart PS. Contributions of antibiotic penetration, oxygen limitation, and low metabolic activity to tolerance of *Pseudomonas aeruginosa* biofilms to ciprofloxacin and tobramycin. Antimicrob Agents Chemother 2003;47:317-23.
Palmer JN. Bacterial biofilms: do they play a role in chronic sinusitis? Otolaryngol Clin N Am 2005;38:1193-1201.
Donlan RM. Biofilms: microbial life on surfaces. Emerg Infect Dis 2002;8:881-90.
Potera C. Forging a link between biofilms and disease. Science 1999;283:1837, 1839.
Post JC, Stoodley P, Hall-Stoodley L, Ehrlich GD. The role of biofilms in otolaryngologic infections. Curr Opin Otolaryngol Head Neck Surg 2004;12:185-90.
Tonnaer EL, Graamans K, Sanders EA, Curfs JH. Advances in understanding the pathogenesis of pneumococcal otitis media. Pediatr Infect Dis J 2006;25:546-52.
Rayner MG, Zhang Y, Gorry MC, Chen Y, Post CJ, Ehrlich GD. Evidence of bacterial metabolic activity in culture-negative otitis media with effusion. JAMA 1998;279:296-9.
Dingman JR, Rayner MG, Mishra S, Zhang Y, Ehrlich MD, Post JC, et al. Correlation between presence of viable bacteria and presence of endotoxin in middle-ear effusions. J Clin Microbiol 1998;36:3417-9.
Perloff JR, Palmer JN. Evidence of bacterial biofilms in a rabbit model of sinusitis. Am J Rhinol 2005;19:1-9.
Chiu A, Antunes M, Feldman M, Cohen N. Dose-dependent effects of topical tobramycin in an animal model of *Pseudomonas sinusitis*. In: Programs and abstracts of the 52nd Annual Meeting of the American Rhinologic Society; Sep. 16, 2006; Toronto, ON, Canada.
Witterick IJ, Kolenda J. Surgical management of chronic rhinosinusitis. Immunol Allergy Clin N Am 2004;24:119-34.
Lieu JE, Piccirillo JF. Methodologic assessment of studies on endoscopic sinus surgery. Arch Otolaryngol Head Neck Surg 2003;129:1230-5.
Lavigne F, Tulic MK, Gagnon J, Hamid Q. Selective irrigation of the sinuses in the management of chronic rhinosinusitis refractory to medical therapy: a promising start. J Otolaryngol 2004;33:10-16.
Yamada et al., "Chitosan Based Water-Resistant Adhesive. Analogy to Mussel Glue", Biomacromolecules 2000, 1 (2), pp. 252-258 (Apr. 13, 2000).
"Protein Polymer Technologies Product Research" dated Mar. 28, 2006, 2 pages, downloaded from the Internet Archive at: http://web.archive.org/web/20060328113942/www.ppti.com/Market/Research.html.
Gross, Charles W., et al., "Autologus Fibrin Sealant Reduces Pain After Tonsillectomy", The Laryngoscope 111, pp. 259-263 (Feb. 2001).
Kitajiri et al., "Relief of Post-Tonsillectomy Pain by Release of Lidocaine From Fibrin Glue", The Laryngoscope 111, pp. 642-644 (Apr. 2001).
Vaiman Michael et al., "Fibrin Sealant Reduces Pain After Tonsillectomy: Prospective Randomized Study", Annals of Otology, Rhinology & Laryngology 115 (7), pp. 483-489 (2006).
Archer, Sanford M. MD, *Nasal Polyps, Nonsurgical Treatment*, eMedicine, dated Oct. 19, 2004, downloaded from the Internet Archive at: http://web.archive.org/web/20041019082359/http://www.emedicine.com/ent/topic334.htm.
Atridox®, Package insert and Carton Label Rev 7 (Feb. 2003).
Kumar et al., "Inhibition of Inflammation and Roflumilast and Dexamethasone in Murine Chronic Asthma", Journal of Pharmacology and Experimental Therapeutics, vol. 307, No. 1, pp. 349-355 (2003).
CollaGenex Atridox® web page, dated Sep. 26, 2004, downloaded from the Internet Archive at: http://web.archive.org/web/20041205004132/collagenex.com/pr_atridox.asp.
Lechapt-Zalcman et al., *Increased expression of matrix metalloproteinase-9 in nasal polyps*, Journal of Pathology, 193:233-241 (2001).

(56) References Cited

OTHER PUBLICATIONS

Kyung, Lee S. et al., *Doxycycline reduces airway inflammation and hyperresponsiveness in a murine model of toluene diisocyanate-induced asthma*, Journal of Allergy and Clinical Immunology [online] (May 2004).

Watelet, J.B. et al., *Matrix metalloproteinases MMP-7, MMP-9 and their tissue inhibitor TIMP-1: expression in chronic sinusitis vs. nasal polyposis*, Allergy, 59:54-60 (2004).

Plateltex, "Reduce fibrosis-Reducing scarring-Autologous Platelets", accessed on Jan. 26, 2010 from: http://www.plateltex.com/lp_reduce_fibrosis.html.

Stoeckli, Sandro J. et al., "A Prospective Randomized Double-Blind Trial of Fibrin Glue for Pain and Bleeding After Tonsillectomy", Laryngoscope 109: pp. 652-655, (Apr. 1999).

Granick Mark MD et al., "Toward a common language: surgical wound bed preparation and debridement", Wound Repair and Regeneration, 14, S1-S10, © the Wound Healing Society, (2006).

Stetter, Christopher et al., "Skin grafting of a chronic leg ulcer with combined Versajet™—V.A.C. therapy", XP-002566870 Case Reports, JDDG, 4:739-742 (2006).

Nagoba, B.S. et al., A Simple and Effective Approach for the Treatment of Chronic Wound Infections Caused by Multiple Antibiotic Resistant *Escherichia coli*, Journal of Hospital Infection, 69:177-180 (2008).

Banin, Ehud et al., "Chelator-Induced Dispersal and Killing of *Pseudomonas aeruginosa* Cells in a Biofilm", Applied and Environmental Microbiology, vol. 72, No. 3, pp. 2064-2069 (Mar. 2006).

Chang, D.M., The Binding of Free Calcium Ions in Aqueous Solution Using Chelating Agents, Phosphates and Poly (Acrylic Acid), JAOCS, vol. 60, No. 3, pp. 618-622 (Mar. 1983).

"Medicine Encyclopedia" M., RLS, Miramistin solution 0.01%, p. 561 ( 2001).

Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide and Xylose-Polyethylene Glycol 400-Hydrogen-Peroxide Pastes Used to Treat Infected Wounds", Antimicrob Agents Chermo, vol. 35, No. 9, pp. 1799-1803 (Sep. 1991).

Sigma-Aldrich Company, Product No. F3879 Fibrinogen Product Information Sheet (2002).

Sigma-Aldrich Company, Product No. T4648 Product Information Sheet (2009).

Sigma-Aldrich Company, Product No. F3879 Fibrinogen Product Specification (2011).

Sigma-Aldrich Company, Product No. 419338 Product Specification (2012).

Sigma-Aldrich Company, Product No. T4648 Product Specification (2013).

*Stedman's Medical Dictionary*, 24th Edition, pp. 1292-1294 (1983).

Phillips, P. et al., "Bacterial Biofilms in wounds", Wound Healing Southern Africa, vol. 1, No. 2, pp. 10-12 (2008).

Pitten et al., "*Efficacy of Cetylpyridinium Chloride Used as Oropharyngeal Antiseptic*", Arzneimittelforschung/Drug Research 51, 7 pp. 588-595 (Jul. 2001).

Birnie et al.,"*Antimicrobial Evaluation of N-Alkyl Betaines and N-Alkyl-N,N-Dimethylamine Oxides with Variations in Chain Length*", Antimicrobial Agents and Chemotherapy, 44 (9), pp. 2514-2517 (Sep. 2000).

Birnie et al., "*Antimicrobial and Diffusional Correlation of N-Alkyl Betaines and N-Alkyl-N,N-Dimethylamine Oxides From Semisolids*", Journal of Pharmaceutical Sciences, 90 (9), pp. 1386-1394 (Sep. 2001).

Steinberg et al., "*Testing a Degradable Topical Varnish of Cetylpyridinium Chloride in an Experimental Dental Biofilm Model*", Journal of Antimicrobial Chemotherapy, 48 (2), pp. 241-24 (Aug. 2001).

Harrington et al., "*Antimicrobial Activity of Gallium against Virulent Rhodococcus equi In Vitro and In Vivo*", Journal of Veterinary Pharmacology and Therapeutics, 29 (2), pp. 121-127 (Apr. 2006).

Stojiljkovic et al., "*Non-Iron Cetylporphyrins: Potent Antibacterial Compounds That Exploit haem/Hb Uptake Systems of Pathogenic Bacteria*", Molecular Microbiology, 31 (2), pp. 429-442 (Jan. 1999).

"Traditional Amine Oxides" BU ICS, Industrial & Home Care, Clariant, Inc. newsletter, Issue 8, pp. 1-7 (Aug. 2010).

Corner, A.M. et al., "C31G, a New Agent for Oral Use with Potent Antimicrobial and Antiadherence Properties", Antimicrobial Agents and Chemotherapy, vol. 32, No. 3, pp. 350-353 (Mar. 1988).

Datsenko B.M., Theory and practice of topical treatment of chronic festering wounds (Problems of therapy using medications), 3 pages (1995).

\* cited by examiner

POLYMERIC SEALANT FOR MEDICAL USE

CROSS REFERENCE TO RELATED APPLICATION

This application is a Divisional of U.S. application Ser. No. 11/704,115, filed Feb. 8, 2007, the disclosure of which is incorporated herein by reference.

THE FIELD OF THE INVENTION

The present invention relates generally to the field of film-forming medical compositions, more specifically to methods and products used to seal mucosa, lessen pain and facilitate recovery by application of a polymeric sealant composition for use in bodily tissues, such as treatment of the throat, tonsils and/or adenoids.

BACKGROUND OF THE INVENTION

Adenoids (pharyngeal tonsils) and tonsils (palatine tonsils) are involved in a number of diseases of the ear, nose, and throat including chronic otitis media with effusion (COME), recurrent acute otitis media (RAOM), adenoiditis, pediatric chronic sinusitis, tonsillitis, pediatric obstructive sleep apnea (OSA), adult OSA, and chronic strep throat. Lingual tonsils can also become infected and be problematic. Treatment for these diseases is primarily achieved first by use of oral medications or, in the case of pediatric and adult sleep apnea through the use of continuous positive airway pressure (CPAP). Otitis media is most often treated primarily with ventilation tube surgery. Failure of these therapies is often followed by surgical removal of the tonsils and/or adenoids to remove them either because they are a harbor for bacteria or as obstructing anatomy. Complications related to these procedures include post-operative bleeding, dehydration, weight loss, peritonsillar abscess, torticilis (neck stiffness), regrowth of tissue, redo surgery due to incomplete removal of tissue, continued COME or RAOM, continued OSA, and occasionally death. Post-operative treatment has traditionally been limited to dietary limitation, rinses, and use of oral antibiotics to prevent post-operative pain and infections.

It has now been discovered that a polymeric film-forming medical sealant composition may be applied to the throat to provide multiple treatment and/or prophylactic functions such as reduction of bleeding, prevention of post-operative infections, tissue protection, reduction in pain, and the like. It is also anticipated that such sealant could be used in the throat, especially on the tonsils, adenoids or the post-operative adenoid remnant to treat otitis media, given the involvement in the disease.

Useful polymeric film-forming medical sealants of the invention may be applied directly to the affected area, are generally resorbable materials which may have residence times of one day or many days or weeks.

SUMMARY OF THE INVENTION

The invention provides a polymeric film-forming sealant for use in medical applications.

Specifically, the invention provides a polymeric film-forming sealant which is useful in applications for treatment and/or post-operative care of the tonsils and adenoids.

More specifically, the invention provides a polymeric film-forming medical sealant useful for application to the tonsils and adenoids, wherein the sealant performs at least one of the following functions, a) inhibits the colonization of bacteria, b) inhibits the binding of bacteria to tissue, c) reduction of tissue morbidity, d) hemostasis, e) coating and protection of tissue during healing, especially postoperative healing, and f) delivery of therapeutic agent(s). In one embodiment, the application of the polymeric sealant of the invention also reduces pain in tissue to which it is applied during treatment or postoperative healing. In another embodiment, the application of the polymeric sealant of the invention also reduces bleeding in tissue to which it is applied.

The polymeric film-forming medical sealant of the invention may further be comprised of a natural therapeutic material such as chitosan, etc. or include at least one therapeutic agent. In one embodiment, the sealant further includes a therapeutic agent selected from the group consisting of analgesics, antihistamines, anti-infective agents, anti-bacteria adhesion agents, anti-fungal agents, biostatic compositions, anti-inflammatory agents, anti-cholinergics, anti-neoplastic agents, cytokines, decongestants, vitamins, peptides, proteins, nucleic acids, immunosuppressors, vasoconstrictors, and mixtures thereof.

The polymeric sealant of the invention may be a viscoelastic material. In another embodiment, the polymeric sealant of the invention may harden after application. In most embodiments, the sealant is a resorbable material having a residence time in vivo of from one day to weeks or months.

The invention also provides a method of treatment for maladies or chronic conditions of the tonsils or adenoids which comprises the step of providing at least one polymeric film-forming medical sealant, and applying it to the tonsils, adenoids or adjacent tissue. The invention further provides a method of postoperative treatment for use after removal of the tonsils or adenoids which comprises the step of providing at least one polymeric film-forming medical sealant, and applying it to the throat, such as to tonsillar fossa.

These terms when used herein have the following meanings:

1. The term "bioresorbable" as used herein, means capable of being absorbed by the body.
2. The term "hemostat" means a device or material which stops blood flow.
3. The term "adhesion" as used herein, refers to the sticking together of a material to tissues with which it is in intimate contact for extended periods.
4. The term "residence time" means the time which the sealant remains in place in vivo.
5. The term "polymeric sealant" means that the sealant is either formed from a synthetic polymer or is a natural polymeric material such as a protein, which is crosslinked.
6. The term "biodegradable" means that the substance will degrade or erode in vivo to form smaller chemical species. Such degradation process may be enzymatic, chemical or physical.
7. The term "biocompatible" means that the substance presents no significant deleterious or untoward effects upon the body.

DETAILED DESCRIPTION OF THE PREFERRED EMBODIMENTS

The following detailed description describes certain embodiments and is not to be taken in a limiting sense. The scope of the present invention is defined by the appended claims.

The polymeric medical sealant provided herein may be used in any manner in which will promote therapeutic improvement. Such uses include, but are not limited to wound management, tissue protection, reduction or elimination of bleeding, reduction of pain, promotion of healing, prevention of infection, and the like. The sealants may also be used as single or combination drug delivery systems for humans or mammals.

The sealant of the invention is a biocompatible composition which adheres to bodily tissues. Most useful sealants are resorbable or degradable, as a non-resorbable or non-degradable adhesive or sealant cannot be used where damaged tissues are not meant to grow together as a permanent or semi-permanent barrier is created if the sealant is not resorbed or degraded.

In one embodiment the sealant may be a polymeric polymer such as silk or silk-elastin polymers which are crosslinked just prior to delivery which can then be sprayed onto the tissue. Useful biodegradable polymers and oligomers include, but are not limited to: poly(lactides), poly(glycolides), poly(lactide-co-glycolides), poly(lactic acids), poly(glycolic acids), polycaprolactones, polyamides, poly(malic acids), polyanhydrides, polyamino acids, polyorthoesters, polyetheresters, polycyanoacrylates, polyphosphazines, polyphosphoesters, polyesteramides, polydiozanones, polyacetals, polyketals, polycarbonates, degradable polyurethanes, polyvinyl pyrrolidones, polyhydroxybutyrates, polyhydoxyvalerates, polyalkylene oxalates, polyalkylene succinates, chitins, chitosans, oxidized celluloses, carboxymethylcellulose, gelatin, agar, and copolymers, terpolymers, blends, and mixtures thereof.

Useful crosslinking materials include, but are not limited to, polyethylene glycol (PEG), chitin, carboxymethylcellulose, and the like, carbodiimides, diisocyanates and/or aldehydes, such as glutaraldehyde or formaldehyde. The material cures to form a hydrogel, which strongly adheres to the tissue.

In another embodiment, the sealant may be a natural protein such as collagen or albumin which is crosslinked, most typically with aldehydes, such as glutaraldehyde or formaldehyde.

In yet another embodiment, the sealant may include a glycol along with a natural protein such as chitin, collagen, agar or albumin. The glycol may be a material such as a polyethylene glycol.

The sealant of the invention may be applied in any known form, such as a gel, one or more flowable liquids that crosslink, polymerize or otherwise alter their consistency to form a sealant, a film strip or sheet material, as a sponge, or as a powder which forms into a sealant or in atomized form may be sprayed onto the tissue.

The polymeric film-forming medical sealants useful for application to the tonsils and adenoids perform at least one of the following functions, a) inhibit the colonization of bacteria, b) inhibit the binding of bacteria to tissue, c) reduction of tissue morbidity, d) hemostasis, e) coating and protection of tissue during healing, f) promotion of healing, and g) reduction of pain. In surgical applications, they may also reduce the formation of post-operative peri-tonsillar abscess formation by reduction of infection and biofilm formation due to the protection of the tissues, and/or inclusion of anti-infective agents. Healing is promoted through wound closure, and maintenance of the wound as a moist wound, which promotes platelet aggregation, and wound closure without excessive scabrous formations, which occur in drier wounds. Acceleration of wound healing and protection of the wound also reduce the chances of infection at the wound site, and resultant pain, inflammation and malodor.

The polymeric film-forming medical sealant may be comprised of a natural therapeutic biomaterial or may include one or more therapeutic agents. The therapeutic agent that may be added to the sealant is not limited in nature, and any agent which is appropriate for medical use may be used. Some common therapeutic agents are those selected from the group consisting of analgesics, antihistamines, anti-infective agents such as anti-bacterial and anti-fungal agents, biostatic compositions, anti-inflammatory agents, anti-cholinergics, antineoplastic agents, cytokines, decongestants, vitamins, peptides, proteins, nucleic acids, vasoconstrictors and mixtures thereof.

Examples of useful additional therapeutic agents include but are not limited to those listed herein. Some useful anti-bacterial agents include aminoglycosides, amphenicols, ansamycins, beta-lactams such as penicillins, ampicillins, cephalosporins, lincosamides, macrolides, nitrofurans, quinolines, sulfonamides, sulfones, tetracycline antibiotics such as chlortricycline, oxytetracycline, demecocycline, doxycycline, democycline, minocycline, methocycline, mecoclycline, methacycline, lymecycline, and the like, vancomycin, and derivatives thereof and mixtures thereof. Examples of anti-fungals include allylamines, imidazoles, polyenes, thiocarbamates, triazoles, and derivatives thereof. Anti-parasitic agents include atovaquone, clindamycin and the like.

In one embodiment, the tetracycline family of materials is preferred therapeutic agents for their combination of anti-inflammatory properties and anti-infective properties. β-lactams that may be suitable for use with the described methods and devices include, but are not limited to, carbacephems, carbapenems, cephalosporins, cephamycins, monobactams, oxacephems, penicillins, and any of their derivatives. Penicillins that may be suitable for use include, but are not limited to, amdinocillin, amdinocillin pivoxil, amoxicillin ampicillin, apalcillin, aspoxicillin, axidocillin, azlocillin, acampicillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G. procaine, penicillin N, penicillin O, penicillin V, penicillin V banzathine, penicillin V hydrabamine, penimepicycline, phenethicillin potassium, piperacillin, pivampicillin propicillin, quinacillin, sulbenicillin, sultamicillin, talampicillin, temocillin, and ticarcillin. In one variation, amoxicillin may be included in the paranasal sinus device. In another variation, the additional agent includes ampicillin. Penicillins combined with clavulanic aid such as Augmentin® (amoxicillin and clavulanic acid) may also be used.

Examples of antifungal agents suitable for use include, but are not limited to, allylamines, imidazoles, polyenes, thiocarbamates, triazoles, and any of their derivatives. In one variation, imidazoles are the preferred antifungal agents. Anti-parasitic agents that may be employed include such agents as atovaquone clindamycin, dapsone, iodoquinol, metronidazle, pentamidine, primaquine, pyrimethamine, sulfadiazine, trimethoprim/sufamethoxazole, trimetrexate, and combinations thereof.

Examples of antiviral agents suitable for use include, but are not limited to acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl) adenine), HPMPG (9-(3-Hydroxy-2-(Phosphonomethoxy) propyl)guanine), PMEG (9-[2-(phosphonomethoxy)ethyl] guanine), HPMPC (1-(2-phosphonomethoxy-3- hydroxypropyl)-cytosine), ribavirin, EICAR (5-ethynl-1-beta-D-ribofuranosylimidazole-4-carbonxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami- -de), LY253963 (1,34-thiadiazol-2-yl-cyanamide), RD3-0028 (1,4-dihydro-2,3-Benzodithiin), CL387626 (4, 4'-bis[4,6-d][3-aminophenyl-N- -, N-bis(2-carbamoylethyl)-sulfonilimino]-1,3,5-triazin-2-ylamino-biphenyl- -2-,2'-disulfonic acid disodium salt), BABIM (Bis[5-Amidino-2-benzimidazoly-1]-methane), NIH351, and combinations thereof.

Examples of steroidal anti-inflammatory agents that may be used in the devices include 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In one variation, budesonide is included in the device as the steroidal anti-inflammatory agent. In another variation the steroidal anti-inflammatory agent may be mometasonefuroate. In yet another variation, the steroidal anti-inflammatory agent may be beclomethasone. In yet a further variation, the steroidal anti-inflammatory agent may be fluticasone propionate.

Suitable nonsteroidal anti-inflammatory agents include, but are not limited to, COX inhibitors (COX-1 or COX non-specific inhibitors) (e.g., salicylic acid derivatives, aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as refecoxib; diaryl-substituted pyrazoles such as celecoxib; indole acetic acids such as etodolac and sulfonanilides such as nimesulide).

The chemotherapeutic/antineoplastic agents that may be used include, but are not limited to antitumor agents (e.g., cancer chemotherapeutic agents, biological response modifiers vascularization inhibitors, hormone receptor blocks, cryotherapeutic agents or other agents that destroy or inhibit neoplasia or tumorigenesis) such as alkylating agents or other agents which directly kill cancer cells by attacking their DNA (e.g., cyclophosphamide, isophosphamide) nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU)), antitumor antibiotics and other compounds that act by binding or intercalating DNA and preventing RNA synthesis (e.g., doxorubicin, daunorubicin, epirubicin, idarubicin, mitomycin-C and bleomycn) plant (vinca) alkaloids and other anti-tumor agents derived from plants (e.g, vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide, and formestane, triazole inhibitors such as letrozole and anastrazole, steroidal inhibitors such as exemastane) antiangiogenic proteins, small molecules, gene therapies and/or other agents that inhibit angiogenesis or vascularization of tumors (e.g., meth-1, meth-2, thalidomide), bevacizumab (Avastin) squalamine, endostatin, angiostatin, Angiozyme, AE-941 (Neoastat), CC-5013 (Revimid), medi-522 (Vitaxin), 2-methoxyestradiol (2ME2, Panzem) carboxyamidotriazole (CAI) combretastatin A4 prodrug (CA4P), SU6668, SU11248, BMS-275291, COL-3, EMD 121974, IMC-1C11, IM862, TNP-470, celecoxib (Celebrex), refecoxib (Vioxx), interferon alpha, interleukin-12 (IL-12) or any of the compounds identified in Science Vol. 298, Pages 1197-1201 (Aug. 17, 2000), which is expressly incorporated herein by reference, biological response modifiers (e.g., interferon, bacillus calmette-guerin (BCG), monoclonal antibodies, interleuken 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine streptocin, taxol or paclitaxel, taxotere, analogs/congeners, derivatives of such compounds, and combinations thereof.

Exemplary decongestants include, but are not limited to, epinephrine, pseudoephedrine, oxymetazoline, phenylephrine, tetrahydrozolidine, and xylometazoline. Mucolytics that may be used include, but are not limited to, acetylcysteine, dornase alpha, and guaifenesin. Antihistamines such as azelastine, diphenhydramine, and loratidine may also be used.

In those instances where it is desirable to remove water from tissue, e.g., to remove fluid from polyps or edematous tissue, a hyperosmolar agent may be employed. Suitable hyperosmolar agents include, but are not limited to, furosemide, sodium chloride gel, or other salt preparations that draw water from tissue or substances that directly or indirectly change the osmolar content of the mucous layer.

Where sustained release or delayed release of the therapeutic agent is desirable, a release agent modifier or other hydrophilic and/or hydrophobic material such as hydroxypropylcellulose, poly(ethylene oxide), polylactic acid hydroxypropyl methylcellulose, ethylcellulose, cellulosic polymers, acrylic polymers, fats, waxes, lipids, polysaccharides, and mixtures thereof may also be present in the medical sealant. The therapeutic agent may also be contained within polymeric microspheres to further delay and/or sustain release of the agent.

The medical sealant may also, if desired include such additives and flavorant where appropriate. Any known flavorant may be used. Examples include anise oil, cinnamon oil, cocoa, menthol, orange or other citrus oils, peppermint oil, spearmint oil, vanillin, fruit flavors and essences, herbal aromatics such as clove oil, sage oil, cassia oil, and the like. The sealant may also include a colorant such as FD & C Red No. 3, FD & C Red No. 20, FD & C Yellow No. 6, FD & C Blue No. 2, D & C Green No. 5, D & C Orange N. 4, D & C Red No. 8, caramel, titanium dioxide, fruit or vegetable colorants such as beet powder, or beta-carotene, turmeric, paprika and others known in the art. The colorant is included to provide visual notification of the presence of the sealant.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, biomedical, and biomaterials arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A method of postoperative treatment for use after removal of the tonsils or adenoids which comprises the step of applying to throat tissue a powder which hardens and crosslinks after application to form a bioresorbable or biodegradable polymeric medical sealant that adheres to such tissue and performs at least one of the following functions: a) inhibits the colonization of bacteria, b) inhibits the binding of bacteria to tissue, c) reduces tissue morbidity, d) hemostasis, e) coats and protects tissue during healing, f) promotes healing, or g) reduces pain, wherein the powder comprises a silk, silk-elastin, poly(malic acid), polyhydroxybutyrate, polyhydroxyvalerate, chitin, chitosan, oxidized cellulose, or agar polymer, copolymer, terpolymer, blend or mixture thereof.

2. The method of treatment according to claim 1 wherein the application of the powder reduces pain in tissue to which it is applied during treatment or postoperative healing.

3. The method of treatment according to claim 1 wherein the powder further includes at least one therapeutic agent selected from the group consisting of analgesics, antihistamines, anti-infective agents, anti-fungal agents, biostatic compositions, anti-inflammatory agents, anticholingerics, antineoplastic agents, cytokines, decongestants, vitamins, peptides, proteins, nucleic acids, immunosuppressors, vasoconstrictors and mixtures thereof.

4. The method of treatment according to claim 1 wherein the powder has a colorant that provides visual confirmation of the sealant present at a surgical site.

5. The method of treatment according to claim 1 wherein the sealant inhibits the colonization of bacteria.

6. The method of treatment according to claim 1 wherein the sealant inhibits the binding of bacteria to tissue.

7. The method of treatment according to claim 1 wherein the powder reduces tissue morbidity in tissue to which it is applied.

8. The method of treatment according to claim 1 wherein the sealant reduces bleeding.

9. The method of treatment according to claim 1 wherein the sealant coats and protects tissue during healing.

10. The method of treatment according to claim 1 wherein the sealant promotes healing.

11. The method of treatment according to claim 1 wherein the sealant performs hemostasis, promotes healing and reduces pain.

12. The method of treatment according to claim 1 wherein the sealant is a crosslinked silk or silk-elastin polymer, or a copolymer, terpolymer, blend, or mixture thereof.

13. The method of treatment according to claim 1 wherein the sealant is a crosslinked chitosan polymer, or a copolymer, terpolymer, blend, or mixture thereof.

14. The method of treatment according to claim 1 wherein the powder comprises a crosslinking material.

15. The method of treatment according to claim 1 wherein the sealant is a polyhydroxybutyrate or polyhydroxyvalerate polymer, or a copolymer, terpolymer, blend, or mixture thereof.

16. The method of treatment according to claim 1 wherein the sealant is a chitin polymer, or a copolymer, terpolymer, blend, or mixture thereof.

17. The method of treatment according to claim 1 wherein the sealant is a poly(malic acid), or a copolymer, terpolymer, blend, or mixture thereof.

18. The method of treatment according to claim 1 comprising applying the powder in atomized form.

19. The method of treatment according to claim 1 wherein the powder forms a pliable barrier upon application.

20. The method of treatment according to claim 1 wherein the sealant is a viscoelastic material.

21. The method of treatment according to claim 1 wherein the sealant has a residence time of at least one day.

22. The method of treatment according to claim 1 wherein the sealant has a residence time of at least one week.

23. The method of treatment according to claim 1 wherein the sealant has a residence time of at least one month.

24. The method of treatment according to claim 1 wherein the sealant is an oxidized cellulose polymer, or a copolymer, terpolymer, blend, or mixture thereof.

25. The method of treatment according to claim 1 wherein the sealant is an agar polymer, or a copolymer, terpolymer, blend, or mixture thereof.

* * * * *

UNITED STATES PATENT AND TRADEMARK OFFICE
CERTIFICATE OF CORRECTION

PATENT NO. : 9,119,896 B2  Page 1 of 1
APPLICATION NO. : 13/323636
DATED : September 1, 2015
INVENTOR(S) : James Britton Hissong et al.

It is certified that error appears in the above-identified patent and that said Letters Patent is hereby corrected as shown below:

Claims

Claim 17; Column 8; Line 30, delete "wherein the sealant is a poly (malic acid), or a copolymer", insert therefor -- wherein the sealant is a poly (malic acid) polymer, or a copolymer --

Signed and Sealed this
Second Day of August, 2016

Michelle K. Lee
*Director of the United States Patent and Trademark Office*